(12) United States Patent
Laver et al.

(10) Patent No.: US 10,806,169 B2
(45) Date of Patent: Oct. 20, 2020

(54) HYDROLYZED PEA PROTEIN-BASED NUTRIENT COMPOSITION

(71) Applicant: Kate Farms, Inc., Santa Barbara, CA (US)

(72) Inventors: Richard Laver, Park City, UT (US); Michelle Laver, Park City, UT (US); Brett Matthews, Santa Barbara, CA (US); William Pickar, Napa, CA (US); David Cole, Peoria, AZ (US); Steven Witherly, Valencia, CA (US); Caroline Witherly, Valencia, CA (US); Vanessa Millovich, Carpinteria, CA (US); Christina Phreaner, Santa Barbara, CA (US)

(73) Assignee: Kate Farms, Inc., Santa Barbara, CA (US)

( * ) Notice: Subject to any disclaimer, the term of this patent is extended or adjusted under 35 U.S.C. 154(b) by 0 days.

(21) Appl. No.: 15/980,355

(22) Filed: May 15, 2018

(65) Prior Publication Data

US 2019/0350245 A1 Nov. 21, 2019

(51) Int. Cl.
*A23L 33/18* (2016.01)
*A23L 33/105* (2016.01)
(Continued)

(52) U.S. Cl.
CPC .............. *A23L 33/18* (2016.08); *A23L 33/105* (2016.08); *A23L 33/12* (2016.08); *A23L 33/15* (2016.08);
(Continued)

(58) Field of Classification Search
None
See application file for complete search history.

(56) References Cited

U.S. PATENT DOCUMENTS 7,875,291 B1 1/2011 Habib et al.
9,801,814 B2 10/2017 Mager et al.
(Continued)

FOREIGN PATENT DOCUMENTS

AU 2017225011 9/2017
CN 105285023 2/2016
(Continued)

OTHER PUBLICATIONS

Muanda, F., et al. "Phytochemical Composition and Antioxidant Capacity of Three Malian Medicinal Plant Parts," Evidence-Based Complementary and Alternative Medicine, 2011, Article ID 674320, 1-8 (2008).
(Continued)

*Primary Examiner* — Aradhana Sasan
(74) *Attorney, Agent, or Firm* — HoustonHogle LLP

(57) ABSTRACT

The present invention discloses a nutritional composition and method of using and making the nutritional composition. The nutritional composition is a hydrolyzed pea protein based nutrient composition for use in both enteral and oral feeding, and provides a non-allergenic diet for providing optimal nutrition to users. The nutritional composition is made from organic and plant-based ingredients. The nutritional composition has pea protein hydrolysates, phytochemical extracts, fatty acids, organic ingredients free of the top eight allergens and corn, and prebiotic fiber. The nutritional composition is provided in liquid form for enteral and/or oral feeding.

16 Claims, 3 Drawing Sheets

(51) Int. Cl.

| | |
|---|---|
| A23L 33/12 | (2016.01) |
| A23L 33/16 | (2016.01) |
| A23L 33/15 | (2016.01) |
| A23L 33/21 | (2016.01) |
| A61K 31/353 | (2006.01) |
| A61K 31/216 | (2006.01) |
| A61K 31/375 | (2006.01) |
| A61K 31/7028 | (2006.01) |
| A61K 31/01 | (2006.01) |
| A61K 31/198 | (2006.01) |
| A61K 31/255 | (2006.01) |
| A61K 31/015 | (2006.01) |
| A61K 9/00 | (2006.01) |
| A61K 36/55 | (2006.01) |
| A61K 36/28 | (2006.01) |
| A61K 38/16 | (2006.01) |
| A61K 31/733 | (2006.01) |
| A61K 31/23 | (2006.01) |
| A61K 36/537 | (2006.01) |
| A61K 36/21 | (2006.01) |
| A61K 36/53 | (2006.01) |
| A61K 33/00 | (2006.01) |
| A61K 33/06 | (2006.01) |
| A61K 33/14 | (2006.01) |
| A23L 33/185 | (2016.01) |

(52) U.S. Cl.
CPC ............ *A23L 33/16* (2016.08); *A23L 33/185* (2016.08); *A23L 33/21* (2016.08); *A61K 9/0019* (2013.01); *A61K 31/01* (2013.01); *A61K 31/015* (2013.01); *A61K 31/198* (2013.01); *A61K 31/216* (2013.01); *A61K 31/23* (2013.01); *A61K 31/255* (2013.01); *A61K 31/353* (2013.01); *A61K 31/375* (2013.01); *A61K 31/7028* (2013.01); *A61K 31/733* (2013.01); *A61K 33/00* (2013.01); *A61K 33/06* (2013.01); *A61K 33/14* (2013.01); *A61K 36/21* (2013.01); *A61K 36/28* (2013.01); *A61K 36/53* (2013.01); *A61K 36/537* (2013.01); *A61K 36/55* (2013.01); *A61K 38/168* (2013.01); *A23V 2002/00* (2013.01)

(56) References Cited

U.S. PATENT DOCUMENTS

| | | | |
|---|---|---|---|
| 2003/0104033 A1 | 6/2003 | Lai et al. | |
| 2007/0042992 A1* | 2/2007 | Frippiat | A61K 31/733 514/54 |
| 2007/0148305 A1* | 6/2007 | Sherwood | A23C 21/08 426/583 |
| 2007/0224323 A1 | 9/2007 | Goldman | |
| 2009/0087519 A1* | 4/2009 | Hundscheid | A21D 2/02 426/74 |
| 2009/0124685 A1* | 5/2009 | Uribe | A61K 31/353 514/456 |
| 2009/0304823 A1 | 12/2009 | Cavin et al. | |
| 2010/0124592 A1* | 5/2010 | Anderson | A23L 11/00 426/270 |
| 2010/0184963 A1* | 7/2010 | Scanlin | A21D 2/165 530/412 |
| 2010/0239712 A1* | 9/2010 | Brooks | A21D 2/165 426/61 |
| 2011/0021421 A1 | 1/2011 | Kiers et al. | |
| 2011/0206787 A1 | 8/2011 | West et al. | |
| 2011/0257089 A1 | 10/2011 | Huisman et al. | |
| 2012/0100257 A1 | 4/2012 | Lambach et al. | |
| 2013/0023468 A1 | 1/2013 | Hofman et al. | |
| 2013/0115329 A1 | 5/2013 | Savant et al. | |
| 2013/0210715 A1* | 8/2013 | Greenberg | A61K 9/0029 514/5.6 |
| 2013/0261183 A1 | 10/2013 | Bhagat | |
| 2014/0113031 A1* | 4/2014 | Lee | A23L 33/105 426/72 |
| 2015/0164985 A1 | 6/2015 | Van Den Braak et al. | |
| 2015/0305359 A1* | 10/2015 | Ao | A23L 33/40 426/2 |
| 2016/0316810 A1* | 11/2016 | Terp | A23C 3/08 |
| 2018/0015032 A1 | 1/2018 | LeBrun-Blashka et al. | |
| 2019/0021387 A1 | 1/2019 | Barata et al. | |
| 2020/0077691 A1 | 3/2020 | Dewille et al. | |

FOREIGN PATENT DOCUMENTS

| | | |
|---|---|---|
| CN | 105533720 | 5/2016 |
| CN | 107259586 | 10/2017 |
| CN | 107684561 | 2/2018 |
| CN | 107692221 | 2/2018 |
| CN | 107997173 | 5/2018 |
| EP | 1 972 346 | 10/2015 |
| JP | 3193095 | 7/2001 |
| JP | 2008/206479 | 9/2008 |
| WO | WO 2007063142 | 6/2007 |
| WO | WO 2013148685 | 10/2013 |
| WO | WO 2017095897 | 6/2017 |

OTHER PUBLICATIONS

Anonymous, "Agave Inulin: All You Need to Know," 1-4 (2016).
Calder, P. C., "Omega-3 polyunsaturated fatty acids and inflammatory processes: nutrition or pharmacology?," British Journal of Clinical Pharmacology, 75(3): 645-662 (2012).
Clinical Trial NCT01298154: Effects of Intact and Hydrolyzed Pea Protein on Food Intake, Glycemic Response and Subjective Appetite http://sunrisechildrenshospital.com/hi/?/21527/Branched-Chain-Amino-Acids-BCAAs-.
Gunnars, K., "How to Optimize Your Omega-6 to Omega-3 Ratio," Jun. 11, 2018 (Jun. 11, 2018); p. 7-9, Section Entitled "Avoid Vegetable Oils High in Omega-6." https://www.healthline.com/nutrition/optimize-omega-6-omega-3-ratio.
Holscher, H.D., "Dietary Fiber and Prebiotics and the Gastrointestinal Microbiota," Gut Microbes, 8(2): 172-184 (2017).
Holsher, H.D., et al., "Agave Inulin Supplementation Affects the Fecal Microbiota of Healthy Adults Participating in a Randomized, Double-Blind, Placebo-Controlled, Crossover Trial 1-3," The Journal of Nutrition, 145(9), 2025-2032 (2015).
International Search Report and Written Opinion of the International Searching Authority, dated Sep. 11, 2019, from International Application No. PCT/US19/31362, filed on May 8, 2019. 11 pages.
International Search Report and Written Opinion of the International Searching Authority, dated Sep. 17, 2019, from International Application No. PCT/US19/34236, filed on May 29, 2019. 10 pages.
Johnson, J.J., "Carnosol: A Promising Anti-Cancer and Anti-Inflammatory Agent," Cancer Letters, 305(1): 1-7 (2011).
Mager, D.R., et al., "Branched chain amino acid requirements in School-Aged children determined by indicator Amino acid oxidation (IAAO)," J. Nutr., 133(11): 3540-3545 (2003).
Maroon, J.C., et al., "Ω-3 Fatty acids (fish oil) as an anti-inflammatory: an alternative to nonsteroidal anti-inflammatory drugs for discogenic pain," Surgical Neurology, 65(4): 326-331 (2006).
Nemzer, B.V., et al., New Insights on Effects of a Dietary Supplement on Oxidative and Nitrosative Stress on Humans, Food Science & Nutrition, 2(6): 828-839 (2014). https://www.ncbi.nlm.nih.gov/pmc/articles/PMC4256589.
Nicolson, L.J., "Acute pancreatitis: should we use antibiotics?," Curr. Gastroenterol. Rep., 13(4): 336-343 (2011).
NSA, "Sunflower Oil" National Sunflower Association, Oct. 8, 2010 (Oct. 8, 2010); entire document. https://web.archive.org/web/20101008154453/https://www.sunflowernsa.com /oil/Linoleic-Sunflower-Oil/.

(56) References Cited

OTHER PUBLICATIONS

Overdiun, J., et al. . Nutralys® pea protein: characterization of in vitro gastric digestion and in vivo gastrointestinal peptide responses relevant to satiety, Food & Nutrition Research, 59: 25622 (2015).

Phillips, E.M., et al., "Peptide-Based Formulas: The Nutraceuticals of Enteral Feeding?," EPCN, 40-45: (2005).

Shyamala, B, N., et al. "Studies on the Antioxidant Activities of Natural Vanilla Extract and its Constituent Compounds through in Vitro Models," Journal of Agric. Food Chem., 55 (19): 7738-7743 (2007).

Textron, "Sunflower Oil, Organic" Textran Product Data Sheet, Dec. 31, 2007 (Dec. 31, 2007); p. 1. https://www.brenntag.com/media/documents/bsi/product_data_sheets/life_science/textron_natural_oils/sunflower_oil_refined-tx008081_pds.pdf.

Wikipedia, "Dietary fiber", Nov. 30, 2017 (Nov. 30, 2017), retrieved on Jul. 8, 2019 from 1-19 https://en.wikipedia.org/w/index.php?title=Dietary_fiber&oldid=812822101; entire document, especially p. 6 para 4.

\* cited by examiner

HYDROLYZED PEA PROTEIN-BASED NUTRIENT COMPOSITION

FIELD OF THE INVENTION

The present invention generally relates to nutrition and the healthcare field. More specifically, the present invention relates to a natural and non-allergenic hydrolyzed pea protein based nutrient composition for use in both enteral and oral feeding.

BACKGROUND OF THE INVENTION

Liquid nutrition supplements are well-known and have been readily available in stores and for medical purposes for many years. These compositions come in various flavors and can be can be consumed in addition to a regular diet, as a replacement for meals in a day, or in lieu of food altogether. Initially, they were developed mostly for use with medical supervision by the elderly, patients recovering from illness, and others who need help putting on or retaining weight, but more have recently been marketed for use by healthy adults.

In the medical field, these compositions are used to treat patients with a variety of ailments that have difficulty digesting foods and have decreased nutrient intake caused by, for example: Gastroesophageal reflux, or rumination; malabsorption due to disorders such as short bowel syndrome, jejunostomy, EOE (eosinophilic esophagitis), celiac disease, cystic fibrosis, Crohn's Disease or disaccharidase deficiency; endocrine dysfunction resulting from conditions such as diabetes mellitus and proteinuria; increased energy requirements of diseases such as bronchopulmonary dysplasia, cystic fibrosis, or hyperthyroidism; and increased energy needs due to trauma, post-operative recovery, nutritional treatment before, during and after cancer treatment, and during times of metabolic stress as seen with neurological disorders such as cerebral palsy and ALS. The above may be characterized generally as Failure to Thrive ("FTT"). Approximately 3-5% of all children admitted to tertiary care centers, and 1% of all children admitted to any hospital, are diagnosed with above ailments or the like.

Pediatric, and infant manufactured nutritional liquids and powders comprising a targeted selection of nutritional ingredients are well known and widely available, some of which may provide a sole source of nutrition, while others may provide a supplemental source. Some of these nutritional liquids utilize pea protein as its main source of protein.

For example, WO 2013148685 to Neal et al describes a nutritional composition including an intact pea protein concentrate as a sole protein source in the nutritional composition because intact pea protein imparts a number of important benefits to the nutritional compositions including excellent texture, sweetness and a smooth and creamy mouthfeel, as well as beneficial effects on glycemic control and response and glucose modulation.

Likewise, US 2003/0104033 to Hernendez et al teaches enteral formulations comprising 40-95 weight % of caseinate and 5-60 weight % of a stabilizing protein, selected from the group of whey protein and one or more vegetable proteins selected from the group of soy, corn, potato, rice and pea, the most preferred vegetable protein being soy protein. The document is concerned with the reduction of creaming in enteral formulae and is silent with respect to digestive properties of hydrolyzed pea protein.

Another example is EP 1 972 346 (WO2007/063142) which discloses a pea-based protein mixture comprising 50 weight % caseinate, 25 weight % whey proteins and 25 weight % pea proteins.

However, these examples disclose the use of intact proteins, do not contemplate the use of pea protein hydrolysates together with other organic plant-based ingredients for patients with impaired gastrointestinal absorption and digestion, are generally whole-food based, nor are they free of common food allergens.

Indeed, food allergies in children are very common—almost 8% of the US children have some type of food allergy. Common allergens consist of milk (including whey, casein, and lactose), wheat, soybeans, eggs, peanuts, tree nuts, fish, shellfish, and corn. As nutrients are necessary for proper growth and development, removing them from a regular diet leads to malnutrition issues. In particular, removal of milks and/or milk proteins, eggs, and soybeans from the diets of children in growth stages presents a serious problem from the perspective of dietetics. Currently, products in markets utilize corn sweeteners, corn starches, synthetic corn derivatives and corn oils, many of which are produced from genetically modified sources. In addition, these products utilize the hydrolyzed protein of milk, whey or casein making their products unavailable to those patients with galactosemia, who are lactose intolerant or have a milk allergy.

Furthermore, conventional peptide formulas do not contain these optimal levels of fatty acids, are often found to have an unfavorable medium chain triglycerides (MCT) and long chain triglycerides (LCT) ratio, and no source of omega 3 fatty acids. Moreover, some of the products are made of synthetic and artificial ingredients. These compositions provide unpleasant taste and odors, preventing them from being taken by patients for a prolonged period, even though they are theoretically free from allergens.

In light of the above-mentioned problems, there is a need for a product that addresses the issues faced by people and patients who rely upon a plant-based, vegan formula free of common allergens and synthetic ingredients which are currently not found in the market. Further, there is a need for a plant-based composition comprising phytonutrients, beneficial fats, that fibers, and are suitable for both oral and enteral administration.

SUMMARY OF THE INVENTION

The present invention discloses a nutritional composition and method of using and making the nutritional composition. The nutritional composition is a composition free of allergens for providing optimal nutrition to users. The nutritional composition is a plant-based, vegan formula free of common allergens and synthetic ingredients. The composition is based on a hydrolyzed pea protein composition for use in both enteral and oral feeding According to the present invention, the nutritional composition constitutes organic and plant-based ingredients. In an embodiment, the nutritional composition comprises at least one of a protein source, one or more phytochemical extracts, one or more fatty acids, one or more organic ingredients free of common allergens (e.g., the top 8 allergens) and corn, and one or more prebiotic fibers. In one embodiment, the protein source is pea protein hydrolysates. In one embodiment, the phytochemical extract are a blend of fruits, vegetables, herbs and spices. In another embodiment, the phytochemical extracts comprise one or more combinations of, a blend of phytochemical extracts from fruits, vegetables, herbs, and spices, organic rosemary extract, potassium citrate, magnesium citrate and potassium chloride. In some embodiments, the blend of phytochemical extracts is sourced from a group of fruits, vegetables, herbs, and spices, comprising one or more concentrates of broccoli sprouts, camu camu, tomato, acai, turmeric, garlic, basil, oregano, cinnamon, elderberry, chokeberry, raspberry, spinach, kale, brussels sprouts, extracts of green arabica coffee bean, green tea, onion, apple, acerola, Japanese pagoda tree (quercetin), blackcurrant, blueberry, bilberry or any combination thereof.

In one embodiment, the fatty acids include organic medium chain triglycerides (MCT) and a balanced blend of omega-6 and omega-3 fatty acids. In another embodiment, the fatty acids include organic sunflower lecithin, organic flax seed oil and organic high linoleic sunflower oil. In one embodiment, the organic ingredient is a non-allergenic ingredient. In another embodiment, the organic ingredient comprises vanilla plant extract.

In one embodiment, the prebiotic fibers include organic inulin (from agave). In another embodiment, the nutritional composition further optionally comprises one or more vitamin and mineral blends, purified water and sea salt.

In exemplary embodiments, the vitamin and mineral blend is selected from a group of dicalcium phosphate, potassium chloride, magnesium chloride, calcium carbonate, choline bitartrate, sodium ascorbate, trisodium citrate, potassium citrate, L-cysteine, Taurine, L-carnitine, inositol, L-tryptophan, DL-alpha-tocopheryl acetate, niacinamide, zinc oxide, ferric orthophosphate, calcium pantothenate, pyridoxine hydrochloride, copper sulfate, magnesium sulfate, riboflavin, thiamine hydrochloride, vitamin A palmitate, beta carotene, folic acid, biotin, chromium picolinate, phytonadione, sodium molybdate, sodium selenite, potassium iodide, vitamin D2 and vitamin B12.

In some embodiments, the nutritional composition further optionally comprises organic brown rice syrup solids, organic agave syrup, organic quinoa flour, organic vanilla flavor and organic milled chia.

In one embodiment, a method for producing the composition is disclosed. At one step, protein slurry is formed by adding and mixing hydrolyzed pea protein to water for ten minutes. At another step, a protein-fat slurry is formed by mixing fat to the protein slurry for five minutes. At another step, all dry ingredients are added to the protein-fat slurry and mixed for approximately five minutes. At another step, agave syrup is added to the mixture and mixed for approximately ten minutes. At another step, the composition is aseptically produced through a microthermics processor. These steps may be performed at ambient temperature and pressure.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The embodiments herein will be better understood from the following detailed description with reference to the drawings, in which.

DETAILED DESCRIPTION OF EMBODIMENTS

Figure 1:
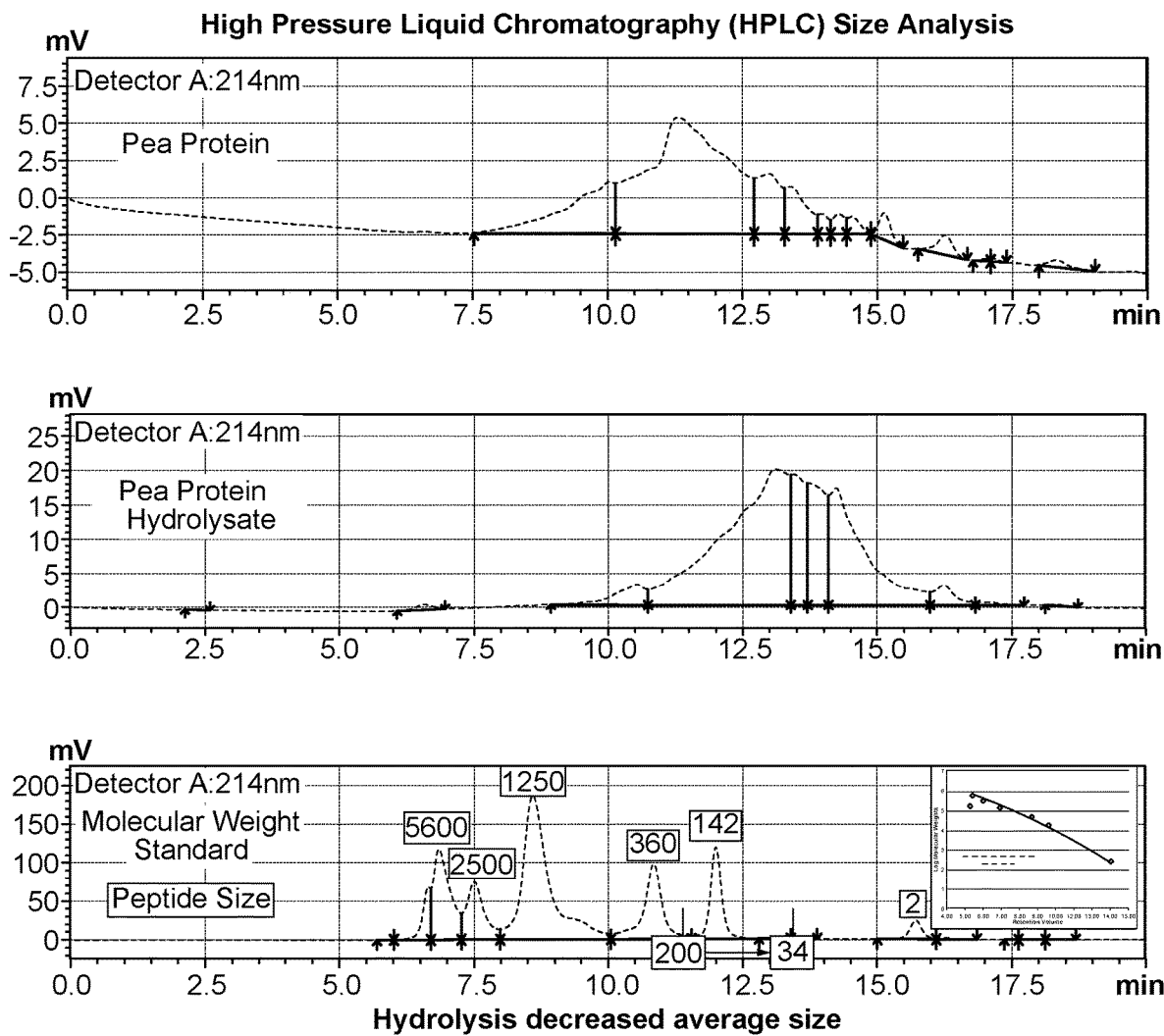
FIG. 1 is a graph illustrating high pressure liquid chromatography (HPLC) size analysis of pea protein in an embodiment of the present invention.

The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

Embodiments of the invention are discussed below with reference to the examples. However, those skilled in the art will readily appreciate that the detailed description given herein with respect to these examples is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention.

The present invention discloses a nutritional composition and method of using said nutritional composition. According to the present invention, the nutritional composition is a non-allergic nutritional composition, which constitutes organic and plant-based ingredients. In one embodiment, the nutritional composition comprises at least one of a protein source, one or more phytochemical extracts, one or more fatty acids, one or more non-allergic organic ingredients, and one or more prebiotic fibers. The organic ingredients are free of corn. The nutritional composition further comprises one or more vitamin and mineral blends, purified water and sea salt. In another embodiment, the nutritional composition further optionally comprises organic brown rice syrup solids, organic agave syrup, organic quinoa flour, organic vanilla flavor and organic milled chia. The nutritional composition is provided in liquid form for enteral and/or oral feeding. The present invention also provides an easily digestible organic plant-based peptide, which is a formulation of a vegan product free from the top eight allergens and corn.

In one embodiment, the protein source is an organic hydrolyzed pea protein. The concentration of organic hydrolyzed pea protein ranges from 6 wt % to 9.2 wt %. In one embodiment, the organic hydrolyzed pea protein constitutes 7 wt % of the total composition and is approximately 100(%) of the total amount of protein in composition. In one embodiment, the organic hydrolyzed pea protein is an enzymatically digested organic intact pea protein.

In one embodiment, the hydrolyzed pea protein is 17% of the size of an intact protein. The hydrolyzed pea protein is produced by reduction from a 200-amino acid chain length down to a 34-amino acid chain length. This process produces a protein composition that is easily digestible. The nutritional composition is a peptide-based composition serving the needs of patients with impaired gastrointestinal absorption and digestion. The ease of digestion of the proteins in pea are very high with a PDCAAS (Protein digestibility-corrected amino acid score) of 98% for the formulation and consequently delivers a full amino acid profile to the patient or user. In addition, branched-chain amino acids in the composition are essential nutrients, where normally the body obtains this type of amino acid from food, especially meat, dairy products, and legumes. In some embodiments, the branched-chain amino acids include leucine, isoleucine, and valine:

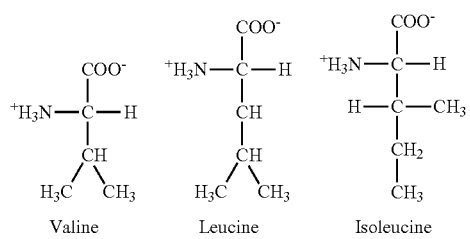

Valine    Leucine    Isoleucine

Branched-chain amino acids stimulate the building of protein in muscle and possibly reduces muscle breakdown. Branched-chain amino acids prevents faulty message transmission in the brain cells with advanced liver disease, mania, tardive dyskinesia, and other types of disease. Some pediatric nutritionists believe children would benefits from higher levels of BCAA's (branched-chain amino acid) than currently recommended. Pea protein is a rich source of BCAA's.

According to the present invention, a 34 aa chain length was chosen based on the influence of the peptide chain length of partial enzymic hydrolysates of protein on nitrogen and amino acid absorption. It was found that nitrogen absorption was significantly slower from the higher chain length peptides. Similarly, longer amino acid residues were not absorbed as well. The chain length of heterogeneous mixtures of peptides affects absorption of nitrogen and individual amino acid residues and suggest that brush border hydrolysis of peptides limits absorption from enzymic hydrolysates of protein. It was inferred that formulas containing shorter length peptides are more readily accessible by the body.

Referring to FIG. 1, a graph illustrating high pressure liquid chromatography (HPLC) size analysis of intact pea protein vs hydrolyzed pea protein in an embodiment of the present invention. Evaluation of intact pea protein displayed a consistent distribution of protein size confirming the control sample is comprised of long chain amino acids that do not vary in length. Conversely, intact pea protein that has undergone enzymatic digestion resulted in varying peptide lengths as is evidenced by the molecular weight standard graph. These data conclude that hydrolysis decreased the average size of the peptide size of existing protein products. In addition, the resultant peptides showed the majority falling into the molecular weight class of 34 amino acid chains. (Product[1] Source: "Peptide-Based Formulas: The Nutraceuticals of Enteral Feeding?" E. Phillips et al., 2005 EPCN October:40-45"). Consequently, enzymatic hydrolysis of intact pea protein results in a "predigested" form of protein resulting in amino acids chains of 34 amino acids, a relative 17% decrease in size as compared to the intact form of the protein.

Figure 2:
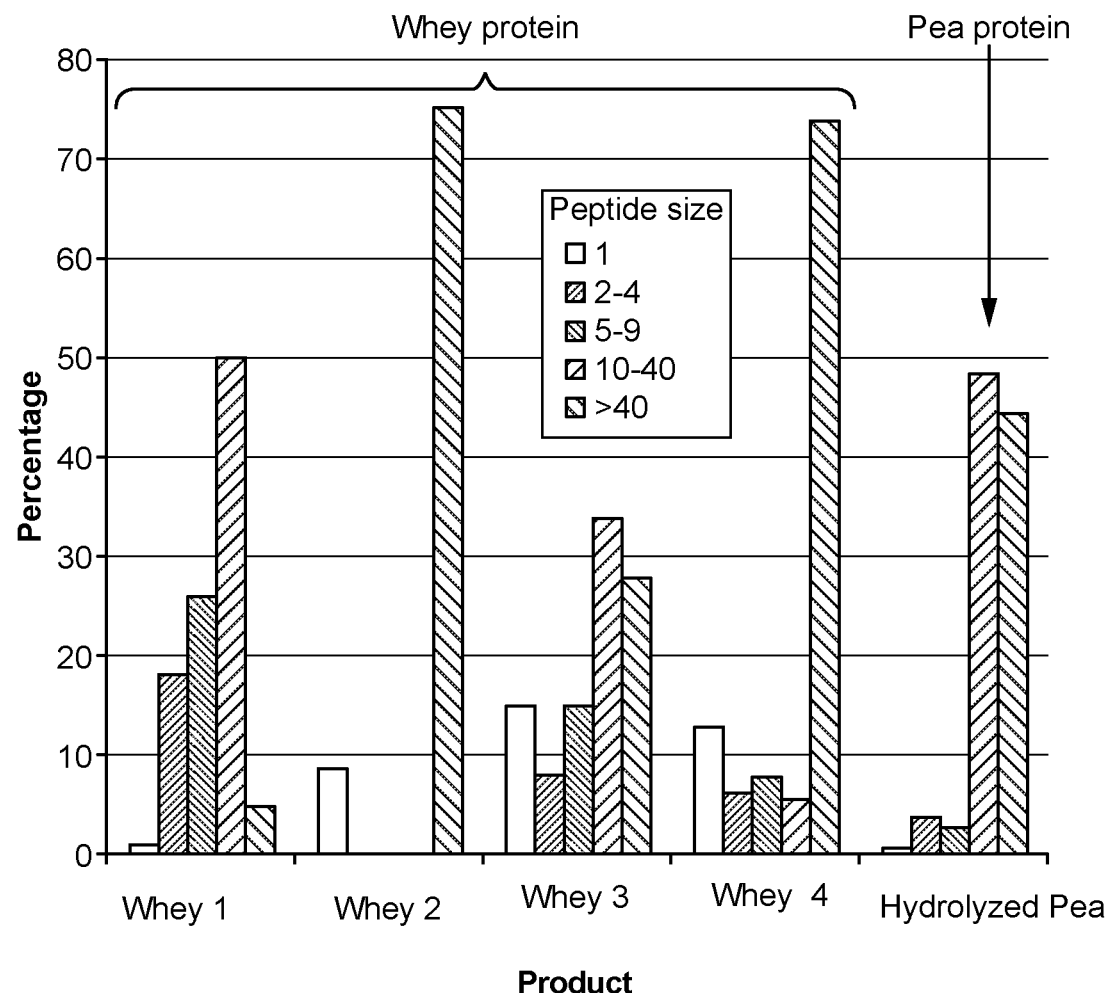
FIG. 2 is a graph illustrating peptide size and distribution comparison of known whey protein products and pea protein product.

Referring to FIG. 2, a graph illustrating peptide size and distribution comparison of known whey protein products and pea protein product. The graph illustrated that the peptide size and distribution of the Pea protein or enzymatically hydrolyzed pea protein is consistent and favourable over the existing whey-based protein products examples 1, 2, 3, and 4. (Product[2] Source: GlycosBio Food Science analysis, 2017). Consequently, pea protein hydrolysate compares favorably to hydrolysis levels seen in whey protein samples. The mean peptide chain for hydrolyzed pea protein in this instance was 34 amino acids long. The results were similar to the results of the hydrolyzed whey protein samples but provided a more consistent result. Studies have shown that pea protein, and specifically peptides, have had positive outcomes in muscle thickening, gastric emptying and heme transport, as compared to the whey protein counterpart. Consistent production of peptide length through the hydrolysis process has the potential to maintain these positive outcomes with consistently shorter peptide lengths being associated with faster nitrogen absorption, which is directly relatable to digestion and absorption of amino acid residues.

In one embodiment, the phytochemical extract is a blend of at least twenty-nine fruits, vegetables, herbs and spices. This natural supplement effects biological changes of oxidative and nitrosative stress markers (free radicals), nitric oxide levels, and cellular metabolic activity. In another embodiment, the phytochemical extracts include organic rosemary extract, blend of phytochemical extracts from fruits, vegetables, herbs, and spices, potassium citrate, magnesium citrate and potassium chloride. In some embodiments, the blend of phytochemical extracts from fruits, vegetables, herbs, and spices comprises any one or more of, concentrates of broccoli sprouts, camu camu, tomato, acai, turmeric, garlic, basil, oregano, cinnamon, elderberry, chokeberry, raspberry, spinach, kale, brussels sprouts, extracts of green arabica coffee bean, green tea, onion, apple, acerola, Japanese pagoda tree (quercetin), blackcurrant, blueberry, bilberry or any combination thereof. The chemical structure of selected phytochemical, such as, glucosinolate, sulforaphane, curcumin, genistein, phenoxodiol (synthetic genistein analog), epigallocatechin gallate (ECGC), lycopene and resveratrol are shown in Table 1.

TABLE 1

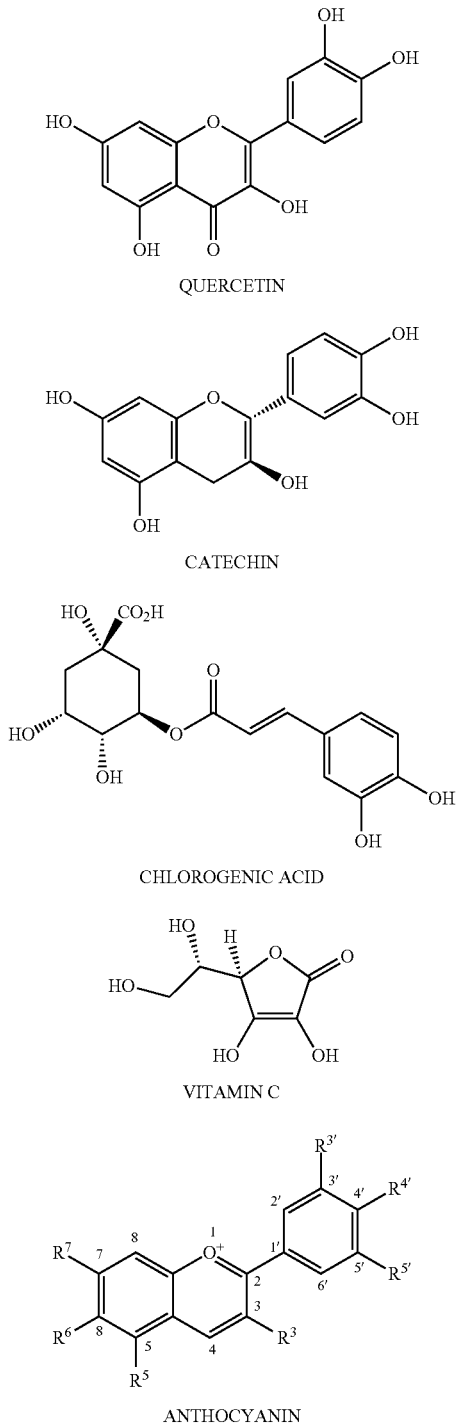

TABLE 1-continued

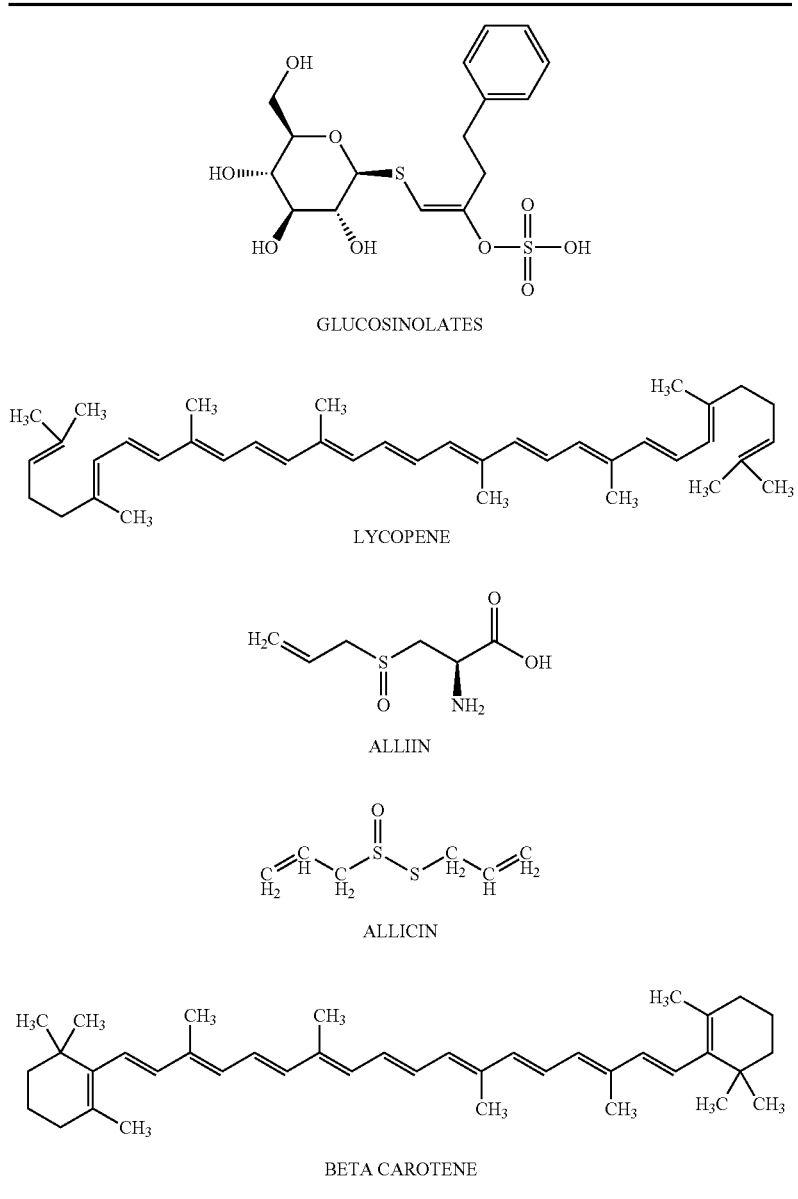

GLUCOSINOLATES

LYCOPENE

ALLIIN

ALLICIN

BETA CAROTENE

In one embodiment, the maximum concentration of organic rosemary extract is 0.05 wt %. In another embodiment, the minimum concentration of organic rosemary extract is 0.03 wt %. In one embodiment, the organic rosemary extract constitutes 0.03 wt % of the total composition. The rosemary-based extract is a natural oxidation-inhibiting product. In one embodiment, the maximum concentration of blend of phytochemical extracts from fruits, vegetables, herbs, and spices is 0.04 wt %. In another embodiment, the minimum concentration of blend of phytochemical extracts from fruits, vegetables, herbs, and spices is 0.03 wt %. In one embodiment, the blend of phytochemical extracts from fruits, vegetables, herbs, and spices constitute 0.04 wt % of the total composition. The blend of phytochemical extracts is sourced from twenty-nine fruits, vegetables, herbs, and spices.

In one embodiment, the potassium citrate constitutes 0.021 wt %, which is obtained from potassium source. In one embodiment, the magnesium citrate constitutes 0.01 wt %, which is obtained from magnesium source. In one embodiment, the potassium chloride constitutes 0.07 wt %., which is obtained from potassium and chloride source.

In one embodiment, the fatty acid contains a balanced blend of essential omega-6 such as sunflower and flax and omega-3 fatty acids such as ALA (alpha-linolenic acid) from flax, and easily digestible medium chain triglycerides (MCT) from coconut oil. In one embodiment, the omega-6 fatty acid is an essential fatty acid. Omega-3 has many anti-inflammatory properties, and MCT is easily digestible, which acts as an immediate energy source via portal vein. In one embodiment, the MCT and long chain triglycerides (LCT) ratio is optimized to 40:60, and the Omega 6 and Omega 3 ratio is formulated to 4:1. In another embodiment, the MCT and LCT ratio is optimized to 50:50 and the omega 6 and omega 3 ratio is 3:1. In one embodiment, the maximum concentration of organic medium chain triglycerides is 2.8 wt %. In another embodiment, the minimum concentration of organic medium chain triglycerides is 2.3 wt %. In one embodiment, the concentration of organic medium chain triglycerides is 2.74 wt %. In some embodiment, the MCT is a form of saturated fatty acid from coconut with medium-chain fats between 6-12 carbons.

In one embodiment, the composition comprises organic sunflower lecithin, organic flax seed oil, and organic high linoleic sunflower oil. In some embodiments, the concentration of organic sunflower lecithin is 0.1 wt %. Lecithin is a naturally occurring substance found in the membranes of living cells. Lecithin is extracted from sunflower seeds.

In one embodiment, the maximum concentration of organic flax seed oil is 1.5 wt %. In another embodiment, the minimum concentration of organic flax seed oil is 1.1 wt %. In one embodiment, the concentration of organic flax seed oil is 1.4 wt %. The organic flax seed oil is a colorless to yellowish oil obtained from the dried, ripened seeds of the flax plant.

In one embodiment, the maximum concentration of organic high linoleic sunflower oil is 3.5 wt %. In another embodiment, the minimum concentration of organic high linoleic sunflower oil is 2.5 wt %. In one embodiment, the concentration of organic high linoleic sunflower oil is 3.00 wt %. The organic high linoleic sunflower oil is a variety of sunflower oil containing nearly 70% polyunsaturated linoleic acid.

In one embodiment, the organic ingredients are non-allergenic ingredients. In another embodiment, the organic ingredients include vanilla plant extract. The vanilla plant extract contains several medicinal properties, which could be useful for tackling several ailments. It is also a rich constituent of flavonoids, alkaloids, glycosides, carbohydrates and several other phytochemicals. The vanilla plant extract also contains both analgesic, antispasmodic, antioxidant and anti-inflammatory properties.

In one embodiment, the vitamin and mineral blend is selected from a group of vitamins and minerals comprised of: dicalcium phosphate, potassium chloride, magnesium chloride, calcium carbonate, choline bitartrate, sodium ascorbate, trisodium citrate, potassium citrate, L-cysteine, taurine, L-carnitine, inositol, L-tryptophan, DL-alpha-tocopheryl acetate, niacinamide, zinc oxide, ferric orthophosphate, calcium pantothenate, pyridoxine hydrochloride, copper sulfate, magnesium sulfate, riboflavin, thiamine hydrochloride, vitamin A palmitate, beta carotene, folic acid, biotin, chromium picolinate, phytonadione, sodium molybdate, sodium selenite, potassium iodide, vitamin D2 and vitamin B12.

In one embodiment, the maximum concentration of vitamin and mineral blend is 1.25 wt %. In another embodiment, the minimum concentration of vitamin and mineral blend is 0.8 wt %. In one embodiment, the concentration of vitamin and mineral blend is 1.22 wt %. The vitamin and mineral blend is a blend of vitamins, minerals and amino acids. In some embodiments, the concentration of the sea salt is 0.03 wt %. The sea salt is obtained from sodium and chloride source.

In one embodiment, the maximum concentration of purified water is 69.5 wt %. In another embodiment, the minimum concentration of purified water is 68 wt %. In one embodiment, the maximum concentration of purified water is 69.14 wt %, which is obtained from a water source.

In one embodiment, the prebiotic fibers include organic inulin (from agave). In one embodiment, the maximum concentration of organic inulin is 1.2 wt %. In another embodiment, the minimum concentration of organic inulin is 1 wt %. In one embodiment, the concentration of organic inulin is 1.20 wt %. The organic Agave inulin is a highly soluble dietary fiber (inulin-type fructan) that provides numerous health benefits. Inulin serves as a "fertilizer" to sustain beneficial bifidobacteria in the large intestine.

The prebiotic fiber is clinically proven to be easy to digest (low gas potential) and promote the growth of good bacteria in the gut such as bifidobacteria. Further, Fecal Actinobacteria and *Bifidobacterium* were enriched 3- and 4-fold after ingestion of agave inulin, a long chain fructo-oligosaccharide (FOS), and *Desulfovibrio* were depleted 40% with agave inulin. Agave inulin tended to reduce fecal 4-methyphenol and pH. A positive association between intakes of agave inulin and *Bifidobacterium* is briefly described herein. Total dietary fiber from agave inulin was positively associated with fecal butyrate and tended to be positively associated with *Bifidobacterium* and was negatively correlated with *Desulfovibrio* abundance. FOS could foster *Bifidobacterium* colony growth, which could also serve as food for less desirable strains of bacteria. Chicory inulin, a source of prebiotic fiber, encourages the growth of *Klebsiella*, which causes problems with intestinal permeability. It also feeds *E. coli* and many *Clostridium* species, which are inharmonious with gut-friendly bacteria.

In one embodiment, the nutritional composition further optionally comprises organic brown rice syrup solids and organic agave syrup. In one embodiment, the maximum concentration of organic brown rice syrup solid is 12 wt %. In another embodiment, the minimum concentration of organic brown rice syrup solid is 6.5 wt %. In one embodiment, the concentration of organic brown rice syrup solid is 10 wt %.

In one embodiment, the maximum concentration of organic agave syrup is 6.5 wt %. In another embodiment, the minimum concentration of organic agave syrup is 2.25 wt %. In yet one embodiment, the concentration of organic agave syrup is 6 wt %. The organic agave syrup is a natural alternative to refined sugars and artificial sweeteners, extracted from the agave plant.

In another embodiment, the nutritional composition further optionally comprises organic quinoa flour in the concentration of 0.02 wt %. The organic quinoa flour is a ground powder from the seeds of *Salvia hispanica*, commonly known as chia, a species of flowering plant in the mint family, lamiaceae, native to central and southern Mexico and Guatemala. In yet another embodiment, the nutritional composition further optionally comprises organic vanilla flavor in the concentration of 1.1 wt %, which is derived from orchid seed pods of the genus *Vanilla*. In another embodiment, the nutritional composition further optionally comprises organic milled chia in the concentration of 0.01 wt %.

The composition should contain a therapeutically effective amount of each ingredient, and also those described in Table 2. The ingredients of the therapeutic composition according to the present invention are summarized in Table 2 below with respect to a description thereof, the active ingredients therein, percentages by weight range for each active ingredient, and the benefits thereof.

TABLE 2

| Ingredient | Minimum Range % | Current % | Maximum Range % | Description |
| --- | --- | --- | --- | --- |
| Organic Agave Syrup | 2.25 | 6.00 | 6.5 | A natural alternative to refined sugars and artificial sweeteners from the agave plant |
| Organic Brown Rice Syrup Solids (20de) | 6.5 | 10.00 | 12 | A natural alternative to refined sugars and artificial sweeteners from the agave plant. |
| Organic Flax Seed Oil | 1.1 | 1.40 | 1.5 | A colorless to yellowish oil obtained from the dried, ripened seeds of the flax plant |
| Organic High Linoleic Sunflower Oil | 2.5 | 3.00 | 3.5 | Variety of sunflower oil containing nearly 70 percent polyunsaturated linoleic acid |
| Organic Hydrolyzed Pea Protein | 6 | 7.00 | 9.2 | Enzymatically digested organic intact pea protein |
| Organic Inulin | 1 | 1.20 | 1.2 | Agave inulin is a highly soluble dietary fiber (inulin-type fructan). Inulin serves as a "fertilizer" to sustain beneficial Bifidobacteria in the large intestine. |
| Organic Medium Chain Triglycerides (Derived from Coconut) | 2.3 | 2.74 | 2.8 | A form of saturated fatty acid from coconut with medium-chain fats that have between 6-12 carbons |
| Organic Milled Chia | 0.01 | 0.01 | 0.01 | A ground powder from the seeds of Salvia hispanica, commonly known as chia, is a species of flowering plant in the mint family, Lamiaceae, native to central and southern Mexico and Guatemala. |
| Organic Quinoa Flour | 0.02 | 0.03 | 0.02 | A ground powder from the seeds of Salvia hispanica, commonly known as chia, is a species of flowering plant in the mint family, Lamiaceae, native to central and southern Mexico and Guatemala. |
| Organic Rosemary Extract | 0.03 | 0.03 | 0.05 | A natural oxidation-inhibiting product |
| Organic Sunflower Lecithin | 0.1 | 0.10 | 0.1 | A naturally occurring substance found in the membranes of living cells. Lecithin is extracted from sunflower seeds. |
| Organic Vanilla Flavor | 1.1 | 1.10 | 1.1 | Flavor derived from orchid seed pods of the genus Vanilla |
| Potassium Citrate | 0.21 | 0.22 | 0.21 | Source of Potassium |
| Purified Water | 68 | 69.14 | 69.5 | Source of water |
| Sea Salt | 0.03 | 0.03 | 0.03 | Source of Sodium and Chloride |
| Blend of phytochemical extracts from fruits, vegetables, herbs, and spices | 0.03 | 0.04 | 0.04 | blend of phytochemical extracts from 29 fruits, vegetables, herbs, and spices. |
| Vitamin and Mineral Blend | 0.8 | 1.22 | 1.25 | Source of 25 vitamins, minerals and amino acids |
| Magnesium Citrate | 0.1 | 0.10 | 0.1 | Source of Magnesium |
| Potassium Chloride | 0.07 | 0.07 | 0.07 | Source of Potassium and Chloride |

In an embodiment, the therapeutic effects of the nutrition composition are numerous. The nutrition composition comprises agave syrup. It contains a higher level of fructose than high fructose corn syrup. An important difference is that fructose is up to twice as sweet as sucrose, and sweeter than high fructose corn syrup. Unlike table sugar or HFCS, fructose does not cause a rapid rise and subsequent large fall in blood glucose levels, which means it has a low glycemic load or glycemic index (GI). The glycemic index is a value assigned to foods based on how slowly or how quickly those foods cause increases in blood glucose levels. The blood glucose levels above normal are toxic and can cause blindness, kidney failure, or increase cardiovascular risk. Food components that are low on the glycemic index (GI) scale tend to release glucose slowly and steadily. Food components that are high on the glycemic index release glucose rapidly. Low GI foods tend to foster weight loss, while foods high on the GI scale help with energy recovery after exercise, or to offset hypo- (or insufficient) glycemia. For an average diet, there are no health problems associated with fructose except for some individuals, who may be fructose intolerant.

Fructose was given GRAS status in 1983 and was reconfirmed in 1996 after a study of the available clinical trials on the effects of fructose consumption. Fructose has a low glycemic index, which can be used to help control blood glucose levels in concern with a total diet plan. Agave syrup is not processed in the same manner as corn syrup. Agave naturally contains inulin, a long chain fructose molecule. Fructose, sometimes known as fruit sugar, exists naturally in fruits and honey as a single unit of fructose. It exists naturally in inulin as a long chain of fructose molecules linked together, similar to the glucose chains in starch. The bonds in inulin can be broken to make free fructose. When a person eats a food containing inulin, the body's enzymes do not break down the inulin. Instead, the inulin is consumed by bacteria in the intestine. The bacteria that consume the inulin tend to be the beneficial bacteria, the same types found in yogurts and various probiotic foods. As the inulin feeds these beneficial organisms, allowing them to outcompete the detrimental intestinal organisms, inulin is labeled a prebiotic and has many health benefits. While fructose could be made by hydrolyzing or breaking the bonds of inulin, it could also be made by using an isomerase enzyme to change glucose into fructose.

In one embodiment, the composition comprising the organic brown rice syrup solid (BRSS) is a natural alternative to refined sugars and artificial sweeteners from the agave plant. Unlike refined table sugar, which causes the body to work harder to absorb the sucrose, brown rice syrup is able to provide the body with fiber, as well as 3% of a user's recommended daily intake of sodium and potassium. As the rice syrup solids are boiled and the liquid is removed, the result is a complex of simple sugars. This facilitates slower absorption of the sugars in rice syrup by the digestive system. This is a huge advantage because in the case of regular table sugar, there is rapid swell in blood sugar level with buildup of excess fat with time. The slower absorption of the sugars also allows the user or patient to maintain their energy and prevents the negative effects of sugar including fatigue, irritability and the desire for more sugar.

All these properties indicate that BRSS also have a low glycemic index. The use of the natural sweetening ability of BRSS is unique in the space of medical grade sole source nutrition. BRSS are a far superior option than maltodextrin, commonly used as a carbohydrate in comparable products. Maltodextrin is used as a thickener, filler or preservative in many processed foods. It is an artificially produced white powder that can be enzymatically derived from any starch but is commonly made from corn, rice, potato starch or wheat. Maltodextrin is also used in carbohydrate supplements that are marketed to athletes and bodybuilders as a way to boost their energy levels. However, consuming maltodextrin leads to spiked blood sugar, suppresses the growth of probiotics, toxically affect several bodily organs and systems, and causes allergic reactions or side effects because it is derived from corn.

In one embodiment, the organic flax seed oil is derived from the extremely nutritious and disease-preventing flax seed. The flax seed oil has a high concentration of healthy omega-3s as fatty acids associated with healthier brains and hearts, better moods, decreased inflammation, and healthier skin and hair. Flax seed oil contains 50% to 60% of omega-3 fatty acids in the form of alpha-linolenic acid (ALA). Flax seed is the richest plant source of the omega($\omega$)-3 fatty acid, i.e. $\alpha$-linolenic acid (ALA). Flax seed oil is low in saturated fatty acids (9%), moderate in monosaturated fatty acids (18%), and rich in polyunsaturated fatty acid (73%). Of all lipids in flaxseed oil, $\alpha$-linolenic acid is the major fatty acid ranging from 39% to 60.42% followed by oleic, linoleic, palmitic and stearic acids, and provides an excellent omega ($\omega$)-6: omega ($\omega$)-3 fatty acid ratio of approximately 0.3:1. Flax seed oil is naturally high in anti-oxidants like tocopherols and beta-carotene. Flax seed oil provides basic nutrition as well as various health benefits in reducing cancer and cardiovascular diseases, lowering LDL-cholesterol and vasodilatory functions. Therefore, flax seed oil could be considered as a functional food. Flax seed oil is emerging as an important functional food ingredient, because of its rich contents of $\alpha$-linolenic acid (ALA, omega-3 fatty acid), lignans, and fiber. Flax seed oil, fibers and flax lignans have potential health benefits such as, in reduction of cardiovascular disease, atherosclerosis, diabetes, cancer, arthritis, osteoporosis, autoimmune and neurological disorders.

The organic high linoleic sunflower oil comprises essential omega-6, impressive fatty acid content, which includes palmitic acid, stearic acid, oleic acid, and linoleic acid. The combination of fatty acids in the body are extremely important to maintain various elements of human health, and sunflower oil could help to maintain the balance. The balance of fatty acids found in sunflower oil, including a substantial amount of linoleic acid (an omega-6 fatty acid) is optimal for patients. Finding a healthy balance between HDL or good cholesterol (omega-3s) and LDL or bad cholesterol is very important to the health of patients. Furthermore, sunflower oil does not contain any saturated fats, which means that it could actually reduce overall cholesterol content in the body. Omega-6 (n-6) polyunsaturated fatty acids (PUFA) in High Linoleic Sunflower Oil (e.g., arachidonic acid (AA)) and omega-3 (n-3) PUFA (e.g., eicosapentaenoic acid (EPA)) are precursors to potent lipid mediator signaling molecules, termed "eicosanoids," which have important roles in the regulation of inflammation.

The composition in embodiments is engineered to have an optimal combination of omega-3 and omega-6 fatty acids which are types of essential fatty acids that are not generated on our own, and have to be obtained from diet. Both are polyunsaturated fatty acids that differ from each other in their chemical structure. There are two critical omega-3 fatty acids, (EPA and DHA), that patients require. Furthermore, vegetarian sources, which the present composition utilizes, such as chia seeds and flax seeds contain a precursor omega-3 (alpha-linolenic acid called ALA) that the body must convert to EPA and DHA. EPA and DHA are the building blocks for hormones that control immune function, blood clotting, and cell growth as well as components of cell membranes.

In contrast, omega-6 foods containing these fatty acids are numerous in modern diets. They are found in seeds and nuts, and the oils are extracted from them. The body also constructs hormones from omega 6 fatty acids. In general, hormones derived from the two classes of essential fatty acids have opposite effects. Those from omega-6 fatty acids tend to increase inflammation (an important component of the immune response), blood clotting, and cell proliferation, while those from omega-3 fatty acids decrease those functions. Both families of hormones must be in balance to maintain optimum health, so there are some omega-6 benefits. Many nutrition experts believe that before we relied so heavily on processed foods, humans consumed omega-3 and omega-6 fatty acids in roughly equal amounts. The imbalance between omega-3 and omega-6 fatty acids may also contribute to obesity, depression, dyslexia, hyperactivity and even a tendency toward violence. Bringing the fats into proper proportion may actually relieve those conditions. The composition of the present invention has a unique 3:1 and 4:1 ratio of omega 6:omega 3 ratio, which facilitates balance of these fatty acids and contributes to the anti-inflammatory effects of them.

The nutrition composition further comprises agave inulin, which is a highly soluble dietary fiber (inulin-type fructan) that provides numerous health benefits. Inulin serves as a "fertilizer" to sustain beneficial bifidobacteria in the large intestine. Inulin is clinically proven to be easy to digest and promotes the growth of good bacteria in the gut such as bifidobacteria. In studies, fecal actinobacteria and *Bifidobacterium* were enriched 3- and 4-fold after ingestion of agave inulin, a long chain fructo-oligosaccharide (FOS), and *Desulfovibrio* was depleted 40% with agave inulin compared with the control. Agave inulin tended to reduce fecal 4-methyphenol and pH. Total dietary fiber from agave inulin has been positively associated with fecal butyrate and tended to be positively associated with *Bifidobacterium* and was negatively correlated with *Desulfovibrio* abundance. Organic inulin could be used in everyday life as a prebiotic and food supplement that stimulates the growth and activity of good bacteria in the body.

The nutrition composition further comprises MCT (Medium-Chain Triglycerides) oil which is quickly and easily digested and provides a relatively large amount of energy to the patient. They (MCT) are associated to stimulate the metabolism and have been identified as a potential weight loss aid. If MCT oil is consumed to increase weight gain, a substantial amount of protein would aid in weight gain. Medium-chain triglycerides are easily absorbed by the gastrointestinal tract and converted into energy by the liver. They are often digested well even by those who cannot digest normal, long-chain fatty acids. MCT are comprised of primarily caprylic and capric fatty acids. MCT help to treat diseases such as cystic fibrosis, and fat malabsorption. They have also been used to add calories to infant and certain other formulas. Unlike other fats, MCT oil benefits because it does not go through the lymphatic system, and instead is transported directly to the liver where it is metabolized so it releases energy like a carbohydrate and creates ketones.

The nutrition composition comprising organic milled chia is a good source of omega-3 fatty acids, which could be used as whole or ground. The organic milled chia is good for intestinal function. There are two critical omega-3 fatty acids, (EPA and DHA), that the body needs. Vegetarian sources, such as chia seeds and flax seeds contain a precursor omega-3 (alpha-linolenic acid called ALA) that the body must convert to EPA and DHA. EPA and DHA are the building blocks for hormones that control immune function, blood clotting, and cell growth as well as components of cell membranes. Chia seeds act as functional foods and may contribute to a better adherence to the dietary treatment in controlling hypercholesterolemia. Chia seeds have an impact on the concentration of total cholesterol (C), LDL-C, HDL-C and lipoprotein. Significant decrease in serum LDL cholesterol was accompanied by a decrease in the concentration of small LDL particles. In addition, systolic and diastolic blood pressure decreases significantly as well as total body weight and BMI.

The nutrition composition further comprises organic quinoa flour, which itself comprises higher dietary fiber content than in other grains. This fiber helps improve intestinal functions. In addition, two flavonoids that have been particularly well studied are quercetin and kaempferol, which are found in large amounts in quinoa. In fact, the quercetin content of quinoa is even higher than typical high-quercetin foods like cranberries. These molecules have anti-inflammatory, anti-viral, anti-cancer and anti-depressant effects. Quercetin, a polyphenolic compound and a major bioflavonoid in the human diet, has anti-inflammatory properties and enhances energy expenditure. Naturally occurring flavonoids inhibit three reverse transcriptases. Quinoa is also gluten-free, making it an optimal choice for patients with celiac or gluten intolerances. Using quinoa instead of typical gluten-free ingredients like refined tapioca, potato, corn and rice flour, dramatically increases the nutrient and antioxidant value of the diet. Henceforth, the composition according to the present invention is gluten-free.

The nutrition composition further comprises organic rosemary extract which has been shown to boost memory, improve mood, reduce inflammation, relieve pain, protect the immune system, stimulate circulation, detoxify the body, protect the body from bacterial infections, prevent premature aging, heal skin conditions, and alleviate digestion problems, including heartburn, intestinal gas (flatulence), liver and gallbladder complaints and loss of appetite. The chemical in rosemary primarily responsible for antioxidation properties is carnosol, a phenolic diterpene also found in mountain desert sage. In addition to being a rich antioxidant, carnosol is also known for its anti-cancer and anti-inflammatory properties. According to a recent article published in the journal Cancer Letters, "Carnosol has been evaluated for anti-cancer property in prostate, breast, skin, leukemia, and colon cancer with promising results". It has also been discovered that carnosol targets cells to reduce inflammation and can also balance androgen and estrogen in the body, reduce cancer risks, increase nerve growth factor healing nerve tissue, and may have a selective toxicity towards cancer cells versus non-tumorigenic cells.

The nutrition composition comprising organic sunflower lecithin is good for heart health. It helps to prevent and reverse damage from coronary disease. Lecithin is essentially an emulsifier of fat which could be used by the body to discard excess fat from the bloodstream. These excess fats include cholesterol and triglycerides, therefore it will help reduce and control levels of cholesterol. A high concentration of linoleic acid present in sunflower lecithin helps to perform the above process. In addition, olive oil has similar levels of linoleic acid. Phospholipids also play a vital essential role for liver health and prevent excessive accumulation of fat.

Further, another advantage of using sunflower lecithin is the extraction process. Sunflower lecithin gets extracted without the need for potentially damaging chemical solvents such as acetone and hexane. Sunflower lecithin is produced through a cold press system, as like deriving oil from olives and similar products. Sunflower lecithin is abundant with essential choline and fatty acids, such as phosphatidylinositol.

The nutrition composition comprising organic vanilla flavor soothes inflammation throughout the body. This is particularly effective for inflammation of the liver, which occurs due to numerous reasons, especially for immunocompromised individuals. Vanillin could help ease arthritis, gout and other inflammatory conditions. Vanilla extract has been evaluated for hepatoprotective activity against paracetamol-induced liver damage in rats. The researchers orally administered an ethanolic extract of *Vanilla planifolia* or a control reference solution to experimental animals with hepatotoxicity induced by paracetamol. It was observed that the plant extract was able to protect the liver against the injury induced by paracetamol in rats. This was proven by the tremendous reduction in serum enzymes alanine aminotransferase (ALT), aspartate aminotransferase (AST), alkaline phosphatase (ALP) and bilirubin. The ethanolic extract of *Vanilla planifolia* has hepatoprotective activity against paracetamol-induced hepatotoxicity in rats. Vanilla extract components were studied for the potential use as antioxidants for food preservation and as nutraceuticals in health supplements. The extract and pure standard compounds were screened to ascertain their antioxidant properties using β-carotene-linoleate and diphenyl picryl hydrazyl (DPPH) in vitro model systems. Interestingly, the study observed and supported the potential use of vanilla bean extracts as antioxidants.

The nutrition composition further comprises potassium citrate, which is an essential nutrient for homeostasis in the body. It works alongside sodium to maintain normal blood pressure. Potassium is known as an electrolyte, helps to maintain a healthy fluid balance in the body. It also helps to transmit electrical pulses to allow proper nerve and muscle function. Potassium citrate is specifically used to help maintain effective body pH.

The nutrition composition further comprises a blend of phytochemical extracts from fruits, vegetables, herbs, and spices, which have been reported to decrease reactive oxygen species (ROS), increase cellular oxygen consumption in blood and mitochondria, decrease extracellular $H_2O_2$, and reduce TNFα-induced inflammatory response in humans. Phytochemicals are the active ingredients that promote whole body health. The extracts do not contain any source ingredients such as, protein, fat, or carbohydrates. The blend may include extracts of green tea and green coffee but does not contain any caffeine. A blend of phytochemical extracts from fruits, vegetables, herbs, and spices represents the latest evolution in the fight against potentially-damaging free radicals. The biological effects of a natural supplement on the changes of oxidative and nitrosative stress markers, as well as cellular metabolic activity, have been clinically observed in the human body. The blend of phytochemical extracts has been reported to decrease ROS, increase cellular oxygen consumption in blood and mitochondria, decrease extracellular $H_2O_2$, and reduce TNFα-induced inflammatory response in humans. Administration of a blend of phytochemical extracts resulted in statistically significant long-term inhibition of mitochondrial and cellular ROS generation by as much as 17% as well as 3.5-times inhibition in extracellular NADPH system-dependent generation of $O_2$, and nearly complete inhibition of extracellular $H_2O_2$ formation. This was reflected in more than two times inhibition of ex vivo cellular inflammatory response and also increases in bioavailable NO concentration. Further, there was measured synergetic, biological effects of a natural supplement on changes in OSM and cellular metabolic activity. The unique design and activity of the plant-based natural supplement, in combination with the newly developed and extended Vitality test, demonstrates the potential of using dietary supplements to modulate OSM and also opens the door to future research into the use of natural supplements for supporting optimal health.

According to the present invention, the biological active compounds and Total Antioxidant Capacity Assay (TAC) for blend of phytochemical extract per serving size of 100 mg is shown in below Table 3.

TABLE 3

| Phytochemical compound | Units | Result |
|---|---|---|
| Glucosinolates | mg | 0.1 |
| Quercetin | mg | 10.8 |
| Lycopene | µg | 43 |
| Chlorogenic acids | mg | 6.7 |
| Vitamin C | mg | 1.2 |
| Catechins | mg | 10.3 |
| Allicin | µg | 10 |
| Alliin | µg | 20 |
| Anthocyanins | mg | 0.5 |
| Vitamin E | µg | 13.4 |
| Beta-carotene | µg | 36.4 |
| Folate | µg | 1.2 |
| Vitamin K | µg | 3.1 |
| Calcium | mg | 0.77 |
| Magnesium | mg | 0.53 |
| Potassium | mg | 4.3 |
| Activity against individual radicals | | |
| Activity against peroxyl radicals | µmol TE | 1070 |
| Activity against hydroxyl radicals | µmol TE | 1511 |
| Activity against peroxynitrite | µmol TE | 110 |
| Activity against superoxide anion | µmol TE | 1337 |
| Activity against singlet oxygen | µmol TE | 417 |
| Total activity | µmol TE | 4445 |

(Source: Phytochemical Composition and Antioxidant Capacity of Three Malian Medicinal Plant Parts Francois Muanda, 1 Donatien Koné, 1 Amadou Dicko, 1, * Rachid Soulimani, 2 and Chafique Younos https://www.ncbi.nlm.nih.gov/pmc/articles/PMC4256589)

The nutrition composition further comprises magnesium citrate to increase fluid in the small intestine to prevent constipation. Magnesium activates over 300 enzyme reactions in the body, translating to thousands of biochemical reactions on a constant basis daily. Magnesium is crucial to nerve transmission, muscle contraction, blood coagulation, energy production, nutrient metabolism, and bone and cell formation.

The nutrition composition further comprises potassium chloride which benefits include relief from stroke, high blood pressure, heart and kidney disorders, and anxiety and stress. It helps in enhancing muscle strength, metabolism, water balance, electrolytic functions, and nervous system. Chloride works with other electrolytes, such as sodium and potassium, to help balance acids and bases in the body. It also helps to move fluid in and out of the cells, which is also essential for preventing dehydration.

Figure 3:
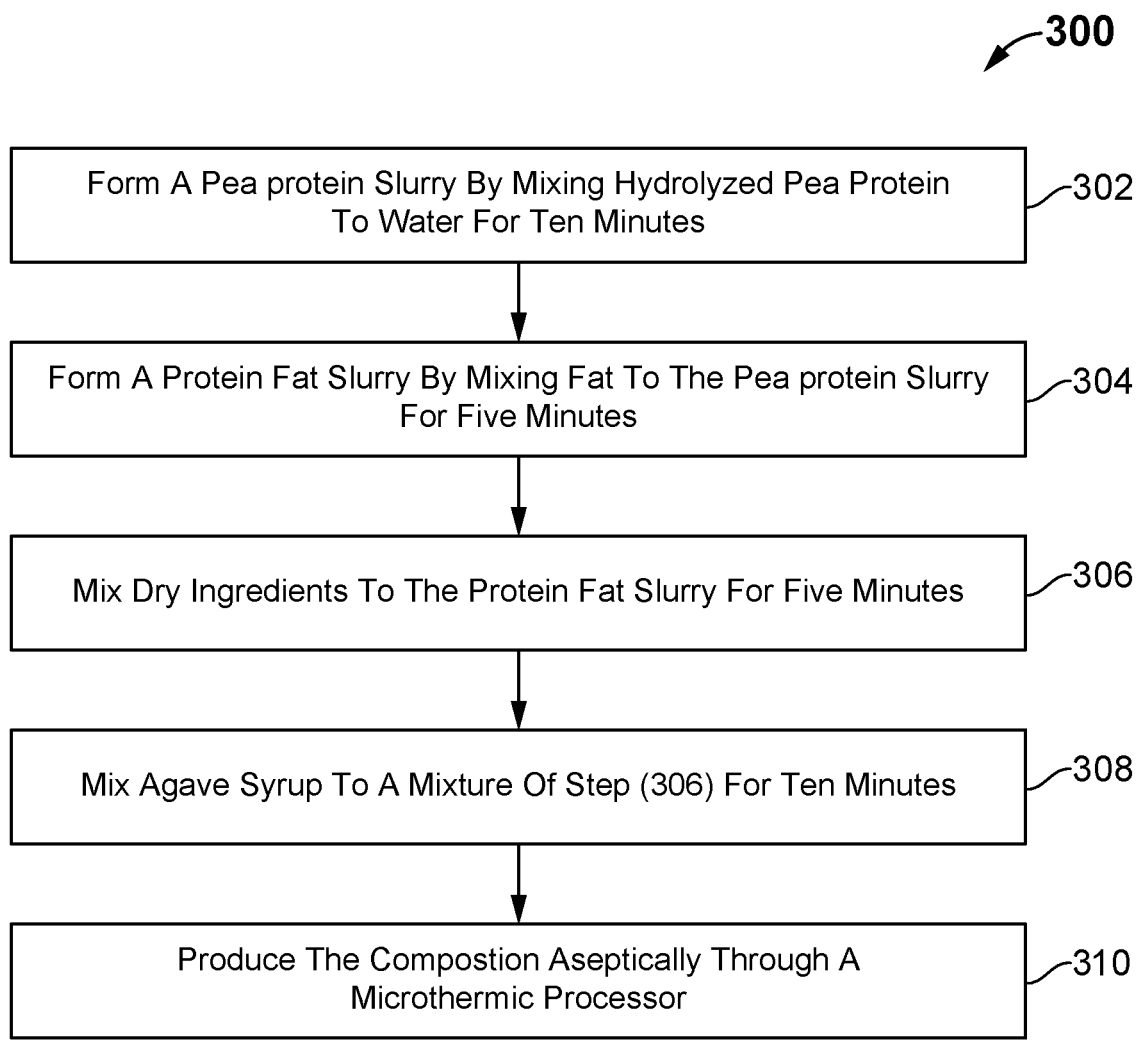
FIG. 3 is a flowchart illustrating a method preparing the nutritional composition in an embodiment of the present invention.

Referring now to FIG. 3, a method 300 for preparing the nutritional composition is illustrated. In an embodiment, the method comprises a protein slurry formed by adding and mixing hydrolyzed pea protein to water for ten minutes, at step 302. At step 304, a protein-fat slurry is formed by mixing fat to the protein slurry for five minutes. At step 306, all dry ingredients are added to the protein-fat slurry and mixed for five minutes. At step 308, agave syrup is added to the mixture and mixed for ten minutes. At step 310, the composition is aseptically produced through a microthermics processor.

The nutritional composition further needs to be heated to a prescribed temperature for a prescribed time period. The specific temperatures and times depend on the food involved. UHT, or Ultra High Temperature treatment takes place in optimized heat exchangers before packaging. This process minimizes heat penetration problems and allows very short heating and cooling times, at the same time minimizing unwanted changes in the taste and nutritional properties of the composition.

The aseptic package has been sterilized prior to filling with UHT (Ultra High Temperature) treated food, resulting in a product which is shelf stable for over 6 months. The Aseptic packaging method passes flat, unformed packaging material through a heated hydrogen peroxide bath. A hydrogen peroxide concentration of 30% is heated at 70° C. for six seconds. Hydrogen peroxide is then eliminated from the packaging material using pressure rollers or hot air.

The environment where food is handled and sealed is free of potentially contaminating bacteria. Further, the filling and sealing machinery are maintained sterile before packaging and during the production process. This could be achieved using hot air and steam or by combining heat treatment with hydrogen peroxide chemical sterilization.

Advantageously, the present invention is entirely plant-based and free of the top eight allergens such as milk, wheat, soybeans, eggs, peanuts, tree nuts, fish and shellfish, corn, and is non-GMO (free of genetically modified organisms). In addition, it contains organic ingredients, optimal fatty acid ratios, oxidation fighting ingredients, anti-inflammatory properties and beneficial fiber. Alternative approaches to the problem include formation of a blended food product. The composition is made with 100% pea protein hydrolysates for optimal digestion.

Although a single embodiment of the invention has been described in the above detailed description, it will be understood that the invention is not limited to the embodiment developed herein, but is capable of numerous rearrangements, modifications, substitutions of parts and elements without departing from the spirit and scope of the invention.

The foregoing description comprises illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions. Although specific terms may be employed herein, they are used only in generic and descriptive sense and not for purposes of limitation. Accordingly, the present invention is not limited to the specific embodiments illustrated herein.

What is claimed is:

1. A nutrient composition in liquid form for enteral and/or oral feeding, comprising:
   pea protein hydrolysate;
   phytochemical extracts including quercetin, catechin, chlorogenic acid, vitamin C, anthocyanin, glucosinolates, lycopene, alliin, allicin, and beta carotene;
   fatty acid-containing components;
   one or more organic ingredients; and
   one or more prebiotic fibers;
   wherein the pea protein hydrolysate constitutes 6 wt % to 9.2 wt% of the total composition, and the pea protein hydrolysate is approximately 100 wt% of the total protein of the mixture;
   wherein the phytochemical extracts are sourced from a blend of fruits, vegetables, herbs and spices; and
   wherein the fatty acid-containing components comprise:
   (a) organic sunflower lecithin constituting 0.1 wt% of the total composition, (b) organic flax seed oil constituting 1.1 wt% to 1.5 wt% of the total composition, and (c) organic high linoleic sunflower oil constituting 2.5 wt% to 3.5 wt% of the total composition.

2. The composition of claim 1, further comprising potassium citrate, magnesium citrate and potassium chloride.

3. The composition of claim 1, wherein the phytochemical extracts are sourced from one or more concentrates of broccoli sprouts, camu camu, tomato, acai, turmeric, garlic, basil, oregano, cinnamon, elderberry, chokeberry, raspberry, spinach, kale, Brussels sprouts, extracts of green arabica coffee bean, green tea, onion, apple, acerola, Japanese pagoda tree, blackcurrant, blueberry, and bilberry.

4. The composition of claim 2, comprising:
   (a) rosemary extract constitutes 0.03 wt % to 0.05 wt % of the total composition,
   (b) blend of phytochemical extracts from fruits, vegetables, herbs, and spices constitutes 0.03 wt % to 0.04 wt % of the total composition,
   (c) potassium citrate constitutes 0.021 wt % of the total composition,
   (d) magnesium citrate constitutes 0.01 wt % of the total composition, and
   (e) potassium chloride constitutes 0.07 wt % of the total composition.

5. The composition of claim 1, wherein the fatty acid-containing components further comprises organic medium chain triglycerides and a balanced blend of omega-6 and omega-3 fatty acids.

6. The composition of claim 5, wherein the medium chain triglycerides constitutes 2.3 wt % to 2.8 wt % of the total composition.

7. The composition of claim 1, wherein the organic ingredients comprises vanilla plant extract.

8. The composition of claim 1, further optionally comprises one or more vitamin and mineral blend, purified water and sea salt.

9. The composition of claim 8, wherein the vitamin and mineral blend is selected from a group of dicalcium phosphate, potassium chloride, magnesium chloride, calcium carbonate, choline bitartrate, sodium ascorbate, trisodium citrate, potassium citrate, L-cysteine, taurine, L-carnitine, inositol, L-tryptophan, DL-alpha-tocopheryl acetate, niacinamide, zinc oxide, ferric orthophosphate, calcium pantothenate, pyridoxine hydrochloride, copper sulfate, magnesium sulfate, riboflavin, thiamine hydrochloride, vitamin A palmitate, beta carotene, folic acid, biotin, chromium picolinate, phytonadione, sodium molybdate, sodium selenite, potassium iodide, vitamin D2 and vitamin B12.

10. The composition of claim 8, comprising:
    (a) vitamin and mineral blend constitutes 0.8 wt % to 1.25 wt % of the total composition,
    (b) sea salt constitutes 0.03 wt % of the total composition, and
    (c) purified water constitutes 68 wt % to 69.5 wt % of the total composition.

11. The composition of claim 1, wherein the prebiotic fiber comprises organic agave inulin.

12. The composition of claim 11, wherein the organic agave inulin constitutes 1 wt % to 1.2 wt % of the total composition.

13. The composition of claim 1, further optionally comprises organic brown rice syrup solids, organic agave syrup organic quinoa flour, organic vanilla flavor and organic milled chia.

14. The composition of claim 13, comprising:
(a) organic brown rice syrup solid constitutes 6.5 wt % to 12 wt % of the total composition,
(b) organic agave syrup constitutes 2.25 wt % to 6.5 wt % of the total composition,
(c) quinoa flour constitutes 0.02 wt % of the total composition,
(d) vanilla flavor constitutes 1.1 wt % of the total composition, and
(e) milled chia constitutes 0.01 wt % of the total composition.

15. The composition of claim 1, wherein the phytochemical extracts further include: vitamin E, folate, vitamin K, calcium, magnesium, and potassium.

16. A nutrient composition in liquid form for enteral and/or oral feeding, comprising:
protein source comprising pea protein hydrolysate which is 100 wt % pea protein hydrolysate based on total protein of the mixture;
phytochemical extracts including quercetin, catechin, chlorogenic acid, vitamin C, anthocyanin, glucosinolates, lycopene, alliin, allicin, and beta carotene;
fatty acid-containing components;
one or more organic ingredients; and
one or more prebiotic fibers comprising organic agave inulin; and
wherein the pea protein hydrolysate constitutes 6 wt % to 9.2 wt % of the total composition, and the pea protein hydrolysate is approximately 100 wt % of the total protein of the mixture;
wherein the phytochemical extracts are sourced from a blend of fruits, vegetables, herbs and spices; and
wherein the fatty acid-containing components comprise:
(a) organic sunflower lecithin constituting 0.1 wt % of the total composition, (b) organic flax seed oil constituting 1.1 wt % to 1.5 wt % of the total composition, and (c) organic high linoleic sunflower oil constituting 2.5 wt % to 3.5 wt % of the total composition.

* * * * *